US010842661B1

(12) United States Patent
Gaylord et al.

(10) Patent No.: US 10,842,661 B1
(45) Date of Patent: Nov. 24, 2020

(54) ORTHOPEDIC THUMB SPLINT AND METHOD FOR STABILIZING THE TRAPEZIOMETACARPAL JOINT OF A USER

(71) Applicant: Medical Specialties Incorporated, Charlotte, NC (US)

(72) Inventors: Eric Lee Gaylord, Weddington, NC (US); Robert Scott Gaylord, Matthews, NC (US)

(73) Assignee: Medical Specialties, Inc., Charlotte, NC (US)

( * ) Notice: Subject to any disclaimer, the term of this patent is extended or adjusted under 35 U.S.C. 154(b) by 373 days.

(21) Appl. No.: 15/879,050

(22) Filed: Jan. 24, 2018

Related U.S. Application Data

(60) Provisional application No. 62/449,787, filed on Jan. 24, 2017.

(51) Int. Cl.
*A61F 5/00* (2006.01)
*A61F 5/058* (2006.01)

(52) U.S. Cl.
CPC .............................. *A61F 5/05875* (2013.01)

(58) Field of Classification Search
CPC ............ A41D 19/015; A41D 16/01582; A41D 19/01588; A41D 19/01582; A61F 5/05875; A61F 5/05866; A61F 5/05841; A61F 5/05; A61F 5/04; A61F 5/01; A61F 5/00; A61F 5/0118; A61F 5/013; A61F 5/10; A61F 5/50; A61F 2007/0037; A61F 2007/0038; A61F 13/10; A61F 13/105; A61F 13/104; A61F 2005/0186; A61F 13/00; A61F 5/30; A61F 5/32; A61F 5/34; A61F 2007/0036; A63B 71/14; A63B 71/141; A63B 71/145; A63B 71/148; A63B 71/08; A63B 71/146; A63B 71/143
USPC ...................................................... 602/21, 22
See application file for complete search history.

(56) References Cited

U.S. PATENT DOCUMENTS

| | | | |
|---|---|---|---|
| 4,632,105 A | 12/1986 | Barlow | |
| 4,953,568 A | 9/1990 | Theisler | |
| 5,356,371 A | 10/1994 | Hubbard | |
| 5,608,912 A * | 3/1997 | Cumberland | .... A41D 19/01582 2/16 |
| 5,787,896 A * | 8/1998 | Sackett | ................. A61F 5/0118 128/880 |
| D473,653 S | 4/2003 | Weaver, II et al. | |
| 7,854,714 B1 * | 12/2010 | Weber | .................. A61F 13/104 128/846 |
| 9,504,282 B1 * | 11/2016 | Frederick | ......... A41D 19/01582 |

(Continued)

*Primary Examiner* — Victoria J Hicks
(74) *Attorney, Agent, or Firm* — Schwartz Law Firm, P.C.

(57) ABSTRACT

An orthopedic thumb splint is adapted for stabilizing a carpometacarpal joint of a user. The exemplary thumb splint includes a flexible fabric splint body having a wrist portion and a generally funnel-shaped thumb portion. The thumb portion defines a narrowed opening for receiving a thumb of the user. A thumb-abducting flexible X-strap is secured to the splint body adjacent the narrowed opening of the thumb portion. The X-strap has first and second diverging distal ends having respective inside surfaces. The inside surface of each distal end includes touch fasteners designed to releasably mate with complementary touch fasteners located on an outside surface of the splint body.

14 Claims, 13 Drawing Sheets

(56) References Cited

U.S. PATENT DOCUMENTS

2003/0191421 A1* 10/2003 Weaver, II ............ A61F 5/0118
                                                                 602/22
2006/0276735 A1* 12/2006 Phelen .................. A61F 5/0118
                                                                 602/21
2017/0354528 A1* 12/2017 Lane ..................... A61F 5/0118

* cited by examiner

ORTHOPEDIC THUMB SPLINT AND METHOD FOR STABILIZING THE TRAPEZIOMETACARPAL JOINT OF A USER

TECHNICAL FIELD AND BACKGROUND OF THE DISCLOSURE

The present disclosure relates broadly and generally to an orthopedic thumb splint and method for stabilizing a carpometacarpal joint of a user; specifically the first carpometacarpal joint. The carpometacarpal (CMC) joints are five joints in the wrist that articulate the distal row of carpal bones and the proximal bases of the five metacarpal bones. The CMC joint of the thumb or the first CMC joint is also known as the trapeziometacarpal (TMC) joint because it connects the trapezium to the first metacarpal bone. The TMC joint is the most important joint connecting the wrist to the metacarpus, and plays an irreplaceable role in the normal functioning of the thumb.

Osteoarthritis of the TMC joint is a common condition that is seen regularly in outpatient occupational therapy and physiotherapy departments. The conservative treatment of choice consists of splinting. The objectives of splinting the TMC joint include stabilizing the joint, reducing pain symptoms as well as enhancing performance of everyday activities—particularly those involving repetitive motion.

The exemplary orthopedic thumb splint of the present disclosure effectively and comfortably braces the thumb while allowing a full range of hand movement. In one embodiment, the present thumb splint may incorporate one or more multi-functional, independently adjustable straps that enable (1) a customized abduction force on the thumb, and (2) a triangulated set of lateral forces at and above the TMC joint. These forces create tension in the strap resulting in compression at the base of the thumb.

SUMMARY OF EXEMPLARY EMBODIMENTS

Various exemplary embodiments of the present disclosure are described below. Use of the term "exemplary" means illustrative or by way of example only, and any reference herein to "the invention" is not intended to restrict or limit the invention to exact features or steps of any one or more of the exemplary embodiments disclosed in the present specification. References to "exemplary embodiment," "one embodiment," "an embodiment," "various embodiments," and the like, may indicate that the embodiment(s) of the invention so described may include a particular feature, structure, or characteristic, but not every embodiment necessarily includes the particular feature, structure, or characteristic. Further, repeated use of the phrase "in one embodiment," or "in an exemplary embodiment," do not necessarily refer to the same embodiment, although they may.

It is also noted that terms like "preferably", "commonly", and "typically" are not utilized herein to limit the scope of the claimed invention or to imply that certain features are critical, essential, or even important to the structure or function of the claimed invention. Rather, these terms are merely intended to highlight alternative or additional features that may or may not be utilized in a particular embodiment of the present invention.

According to one exemplary embodiment, the present disclosure comprises an orthopedic thumb splint adapted for stabilizing a carpometacarpal joint of a user. The exemplary thumb splint comprises a flexible fabric splint body having a wrist portion and a generally funnel-shaped thumb portion. The thumb portion defines a narrowed opening for receiving a thumb of the user. A thumb-abducting flexible generally X-shaped strap ("X-strap") is secured to the splint body adjacent the narrowed opening of the thumb portion. The X-strap comprises first and second diverging (and downwardly angled) distal ends having respective inside surfaces. The inside surface of each distal end comprises touch fasteners designed to releasably mate with complementary touch fasteners located on an outside surface of the splint body. The exemplary touch fasteners may comprise hook and loop, or other suitable means. In one exemplary implementation, an adjustable abduction force is applied to the thumb of the user by pulling the X-strap outwardly from the thumb portion and downwardly towards the wrist portion of the splint body, and then mating the complementary touch fasteners of the distal ends and splint body to releasably attach the distal ends at a base of the thumb.

The term "touch fasteners" refers broadly to any complementary male/female fasteners (e.g., hook and loop fasteners) which releasably attach together by urging or applying one fastener onto the other. In one embodiment, the touch fasteners may be inherently or integrally formed with a fabric material. Other mechanical fasteners may be used in the present thumb splint including (e.g.) buckles, clips, clasps, and the like.

According to another exemplary embodiment, the X-strap further comprises a proximal looped end extending around the thumb portion adjacent the narrowed opening.

According to another exemplary embodiment, the X-strap is permanently affixed to the splint body at a single attachment point on a web side of the thumb portion. The term "permanently affixed" as used herein means attached in a manner intended to be non-detachable, such as by sewing.

According to another exemplary embodiment, the X-strap further comprises an intermediate inside fastener patch located between the first and second distal ends.

According to another exemplary embodiment, the wrist portion of the splint body comprises first and second cooperating flexible closure straps having respective free ends adapted to releasably wrap around a wrist of the user.

According to another exemplary embodiment, the splint body comprises an inverted T-shaped non-stretch region located between the first and second closure straps, and extending upwardly along the thumb portion towards the narrow opening. The term "non-stretch" means having limited, reduced, or no fabric stretch compared to one or more immediately adjacent areas of the splint body.

According to another exemplary embodiment, the splint body is substantially stretchable in adjacent areas outside of the non-stretch region. The term "substantially stretchable" means having increased or greater fabric stretch (in one or more directions) as compared to the fabric stretch within the non-stretch region.

According to another exemplary embodiment, the splint body comprises added padding in the non-stretch region.

According to another exemplary embodiment, the free ends of the first and second closure straps comprise respective touch fasteners.

According to another exemplary embodiment, the first closure strap comprises an intermediate inside patch of pre-hold touch fasteners spaced apart from its free end, and adapted to form a preliminary (and releasable) holding point when wrapping the first and second closure straps together around the wrist of the user.

According to another exemplary embodiment, the free end of the first closure strap comprises a non-stretch nylon hook tab.

According to another exemplary embodiment, a removable semi-rigid stay pod is adapted for placement on the outside surface of the splint body proximate the base of the thumb. The exemplary stay pod may comprise an internal metal body sandwiched between outside fabric layers, and may be semi-rigid, or semi-rigid and bendable to a desired fixed curvature, or rigid, or rigid and bendable to a desired fixed curvature.

According to another exemplary embodiment, the stay pod comprises touch fasteners adapted to releasably mate with complementary touch fasteners of the splint body.

According to another exemplary embodiment, the distal ends of the X-strap comprise respective non-stretch nylon hook tabs.

In yet another exemplary embodiment, the present disclosure comprises a method for stabilizing a carpometacarpal joint of a user. The exemplary method includes applying the present orthopedic thumb splint to the thumb of a user, as described further herein.

BRIEF DESCRIPTION OF THE DRAWINGS

Exemplary embodiments of the present disclosure will hereinafter be described in conjunction with the following drawing figures, wherein like numerals denote like elements, and wherein.

DESCRIPTION OF EXEMPLARY
EMBODIMENTS AND BEST MODE

The present invention is described more fully hereinafter with reference to the accompanying drawings, in which one or more exemplary embodiments of the invention are shown. Like numbers used herein refer to like elements throughout. This invention may, however, be embodied in many different forms and should not be construed as limited to the embodiments set forth herein; rather, these embodiments are provided so that this disclosure will be operative, enabling, and complete. Accordingly, the particular arrangements disclosed are meant to be illustrative only and not limiting as to the scope of the invention, which is to be given the full breadth of the appended claims and any and all equivalents thereof. Moreover, many embodiments, such as adaptations, variations, modifications, and equivalent arrangements, will be implicitly disclosed by the embodiments described herein and fall within the scope of the present invention.

Although specific terms are employed herein, they are used in a generic and descriptive sense only and not for purposes of limitation. Unless otherwise expressly defined herein, such terms are intended to be given their broad ordinary and customary meaning not inconsistent with that applicable in the relevant industry and without restriction to any specific embodiment hereinafter described. As used herein, the article "a" is intended to include one or more items. Where only one item is intended, the term "one", "single", or similar language is used. When used herein to join a list of items, the term "or" denotes at least one of the items, but does not exclude a plurality of items of the list.

For exemplary methods or processes of the invention, the sequence and/or arrangement of steps described herein are illustrative and not restrictive. Accordingly, it should be understood that, although steps of various processes or methods may be shown and described as being in a sequence or temporal arrangement, the steps of any such processes or methods are not limited to being carried out in any particular sequence or arrangement, absent an indication otherwise. Indeed, the steps in such processes or methods generally may be carried out in various different sequences and arrangements while still falling within the scope of the present invention.

Additionally, any references to advantages, benefits, unexpected results, or operability of the present invention are not intended as an affirmation that the invention has been previously reduced to practice or that any testing has been performed. Likewise, unless stated otherwise, use of verbs in the past tense (present perfect or preterit) is not intended to indicate or imply that the invention has been previously reduced to practice or that any testing has been performed.

Figure 1:
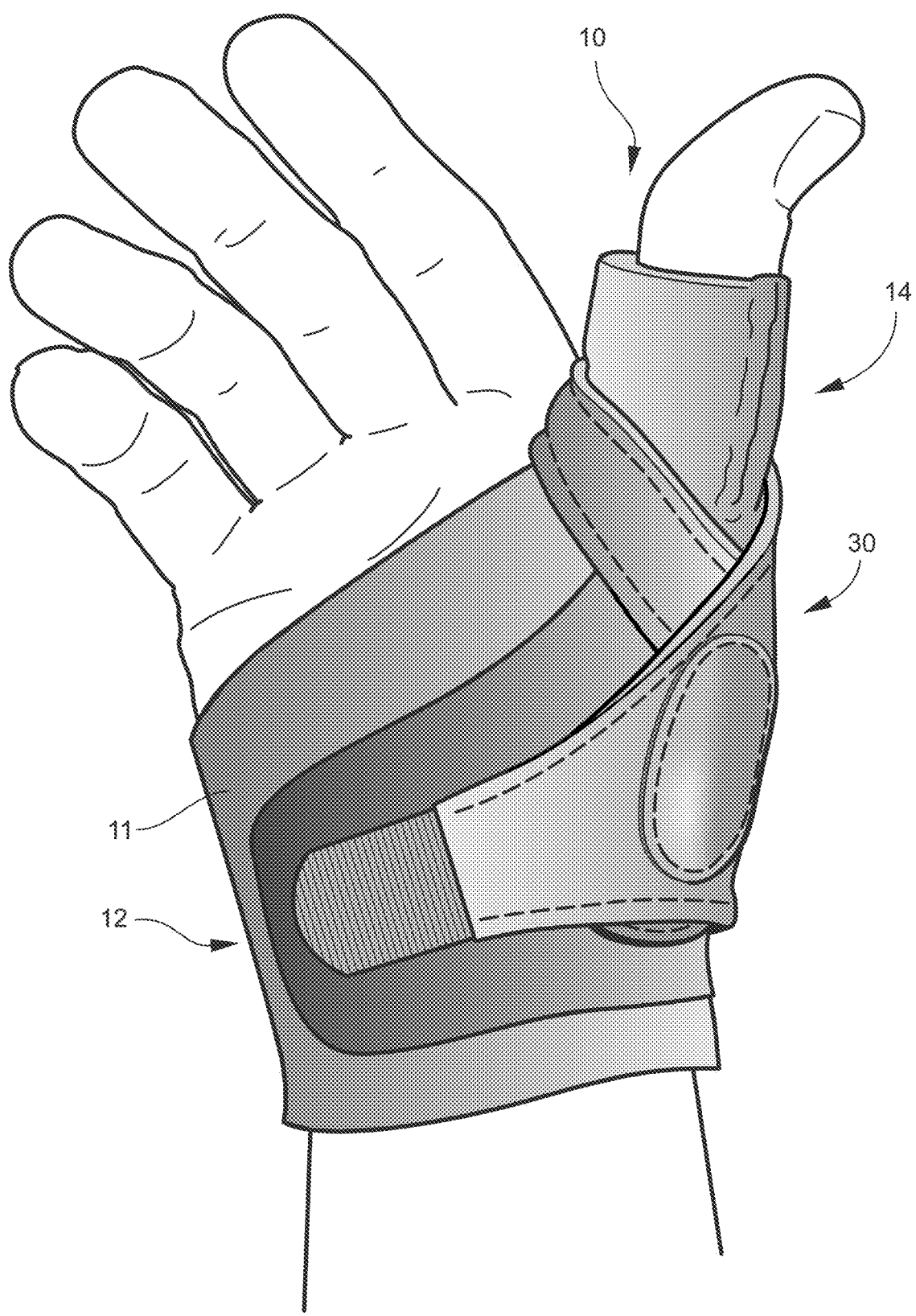
FIGS. 1 and 2 are perspective views showing the present orthopedic thumb splint applied to a hand of the user.
Figure 2:
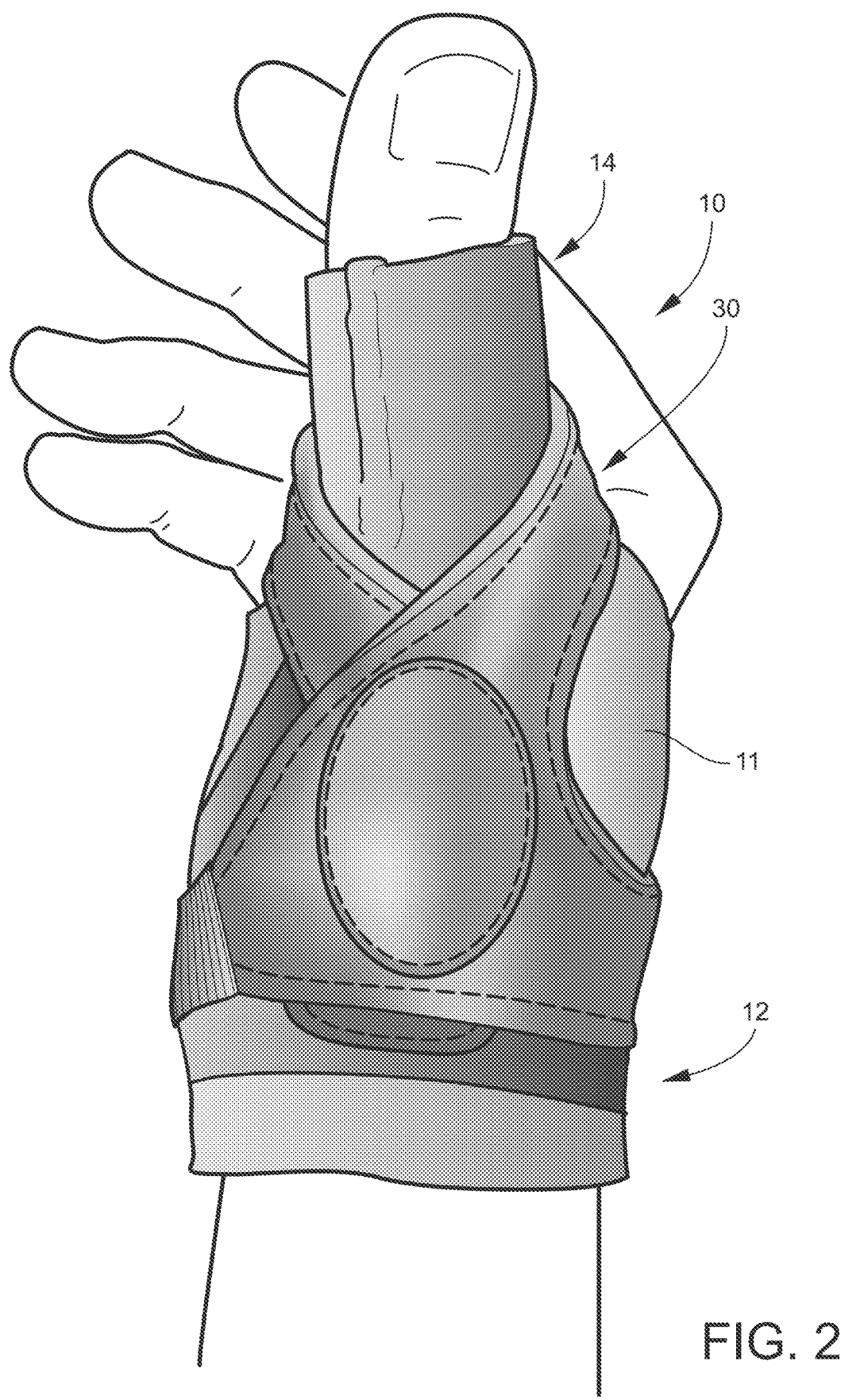
Figure 3:
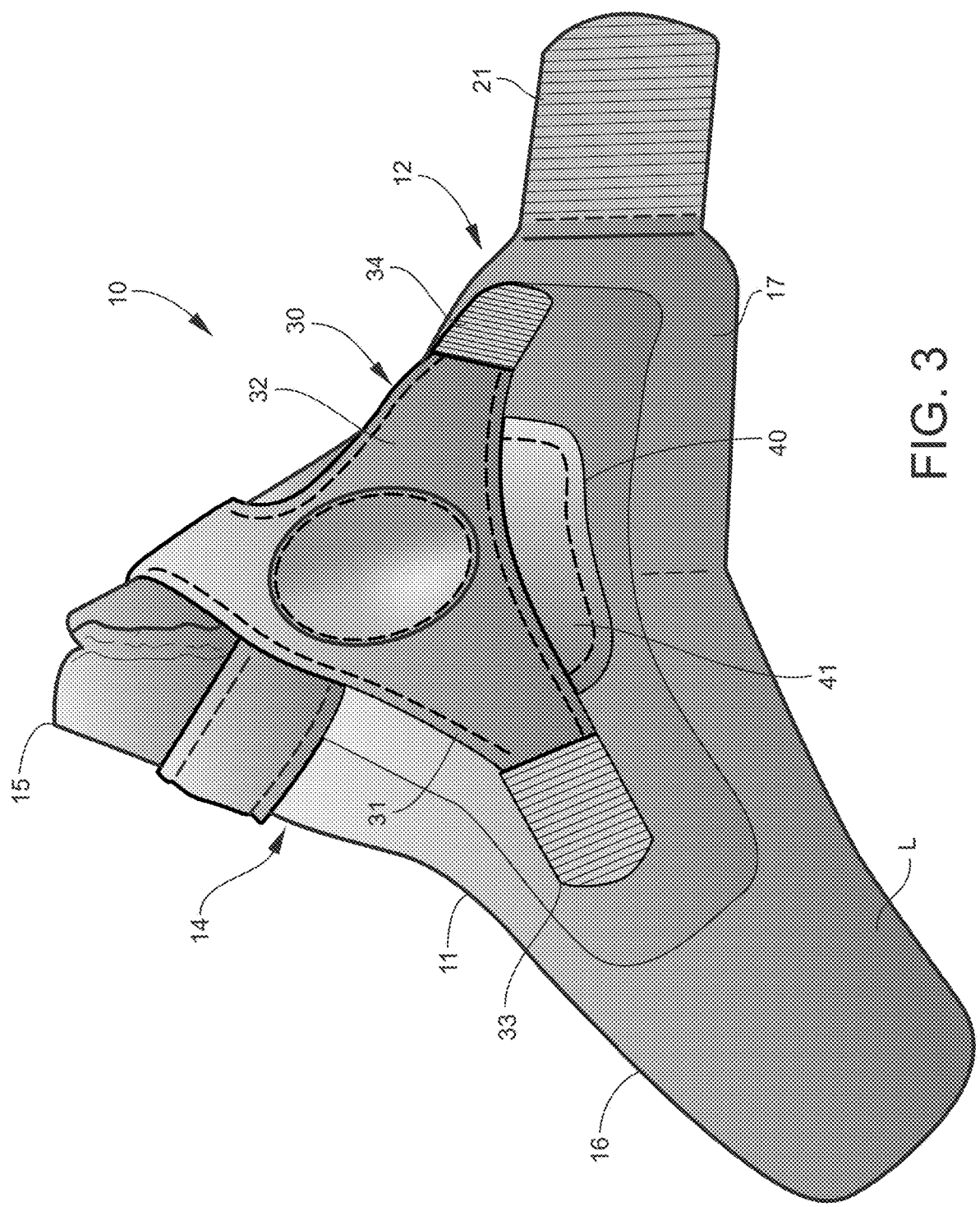
FIG. 3 is an outside perspective view of the exemplary thumb splint removed from the hand and showing the flexible closure straps of the wrist portion extended.
Figure 4:
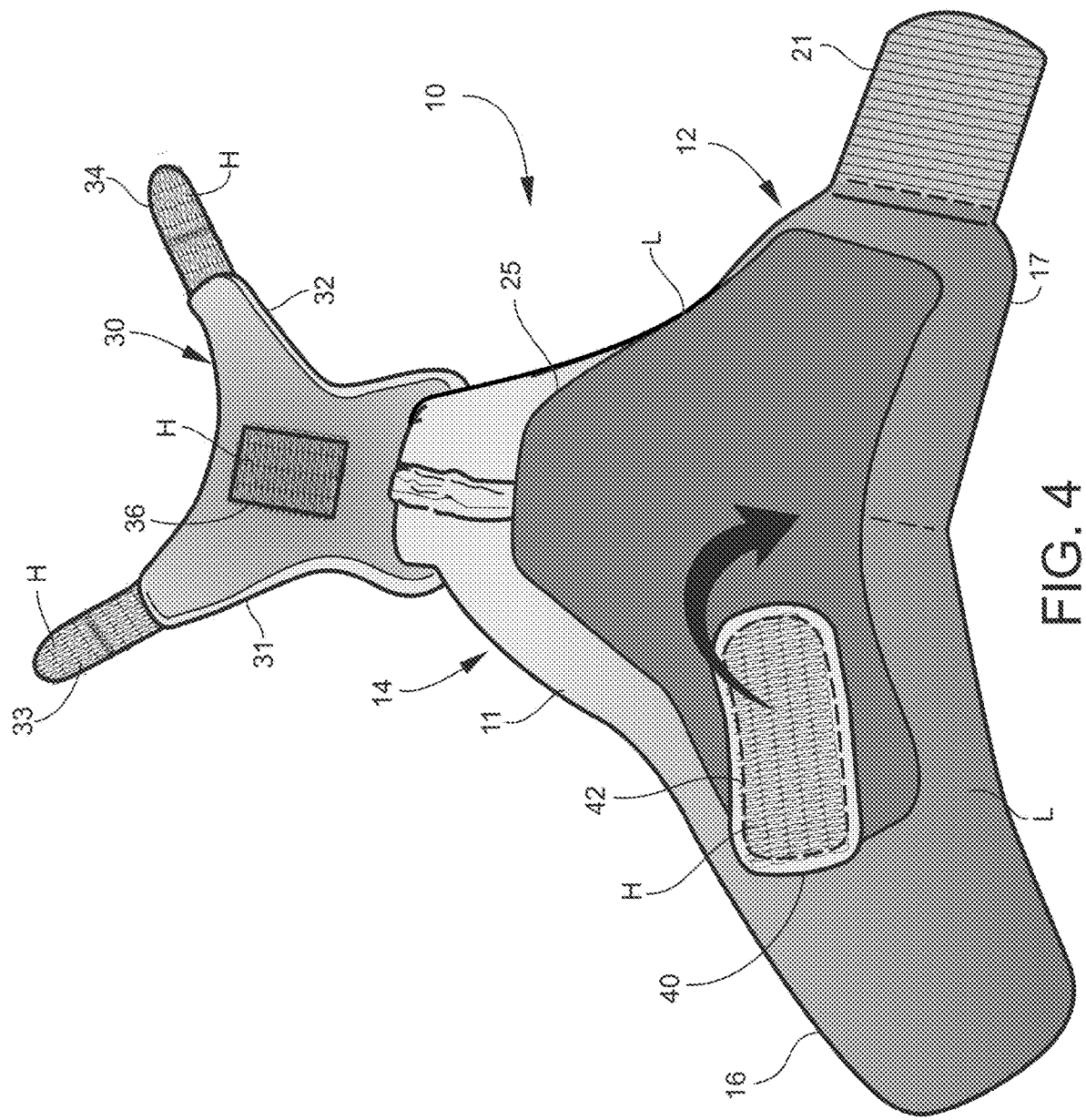
FIG. 4 is a further outside perspective view of the exemplary thumb splint, and showing the X-strap and stay pod pulled away from the splint body.

Referring now specifically to the drawings, an orthopedic thumb splint according to one exemplary embodiment of the present disclosure is illustrated in FIGS. 1 and 2, and shown generally at broad reference numeral 10. The exemplary thumb splint 10 incorporates various structural elements and features designed to control or influence the position of the metacarpal bone for the purpose of stabilizing the first carpometacarpal (CMC) joint—or trapeziometacarpal (TMC) joint. The exemplary thumb splint 10 effects targeted compression at the base of the thumb with applied force and location adjustability, while simultaneously enabling independently adjustable thumb abduction at the TMC joint. In exemplary embodiments, the present thumb splint 10 may be manufactured primarily from a hypoallergenic foam-based, stretch laminate having exterior loop fabric.

As best shown in FIGS. 1-5, the orthopedic thumb splint 10 comprises a flexible fabric body 11 that is readily applied to and removed from the hand of the user, and allows substantially unrestricted wrist and hand function. The exemplary splint body 11 comprises a wrap-around wrist portion 12 and an inverted funnel-shaped thumb portion 14. The thumb portion 14 defines a narrowed opening 15 for receiving the thumb of the user. The exemplary wrist portion 12 includes cooperating first and second stretchable elastomeric closure straps 16, 17 intended to wrap around the wrist at the base of the hand. The closure straps 16, 17 enable the splint 10 to be comfortably and adjustably positioned on the hand in the desired thumb-abducted position, and allow the user substantial freedom (range of motion) to grasp and handle objects. The wrist and thumb portions 12, 14 may be integrally formed together of a stretchable elastomeric fabric having an inherent "looped" fabric surface capable of releasable mating with complementary nylon hook fasteners at multiple locations on the splint body 11.

The second closure strap 17 of wrist portion 12 has a distal-end, non-stretch, nylon fastener tab 21 comprising closely spaced rows of inside hook fasteners "H". The hook fasteners "H" releasably attach to the outside loop fabric surface "L" of the first closure strap 16, thereby allowing circumferential adjustment of the straps 16, 17 around the wrist and hand of the user. Additionally, an intermediate pre-hold fastener patch 22 of closely spaced nylon hook fasteners "H" may be located on an inside surface of the second closure strap 17, and may releasably attach at an intermediate point on the loop fabric surface "L" of the first closure strap 16. The pre-hold fastener patch 22 may facilitate preliminarily, single-hand application of the splint body 11 to the thumb and hand prior to custom tightening (tensioning) the closure strap 17 using the inside hook fasteners "H" of distal tab 21. In alternative exemplary embodiments, the wrist portion 12 of splint body 11 may comprise only a single closure strap with releasable touch fasteners, or may comprise a continuous slip-on stretchable fabric band made in various sizes to properly fit the hand and wrist of the particular user.

Figure 5:
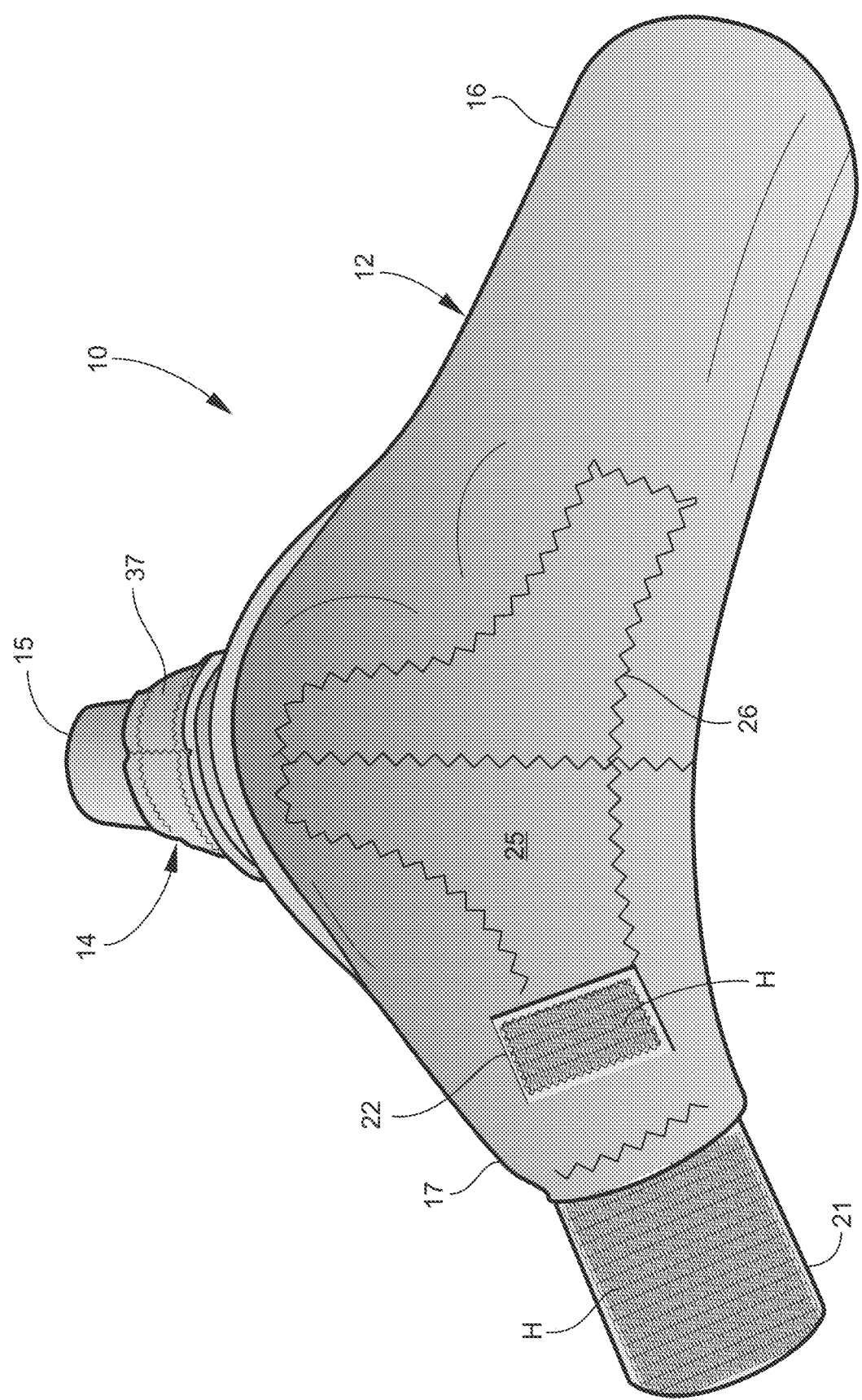
FIG. 5 is an inside perspective view of the exemplary thumb splint removed from the hand and showing the flexible closure straps of the wrist portion extended.

As best shown in FIG. 5, the exemplary fabric splint body 11 may further incorporate an inverted T-shaped non-stretch region 25 located between the first and second closure straps 16, 17, and extending upwardly along the thumb portion 14 towards the narrow opening 15. The non-stretch region 25 may be formed along stitch lines 26 by conventional sewing, and may comprise additional fabric padding or thickness intended to reside immediately adjacent an outside and base of the thumb proximate the TMC joint. Stretch within this region 25 of the splint body 11 may be negated entirely in all directions, or may be reduced in one or more directions as compared to immediately adjacent areas of the wrist and thumb portions 12, 14. The exemplary splint body 11 remains stretchable in all adjacent areas outside of the non-stretch region 25. The width of the non-stretch region 25 at its three spaced ends may be between 1-2 inches.

In the exemplary splint 10 shown, a flexible, multifunction, elastomeric X-strap 30 is looped around the funnel-shaped thumb portion 14 of the flexible body 11, and is permanently attached (e.g., by sewing) on a web side of the thumb portion 14 just below the narrowed opening 15. The X-strap 30 has two diverging and slightly (downwardly) angled distal ends 31, 32 with respective fastener tabs 33, 34 comprising nylon hook fasteners "H" designed to releasably mate with the outside loop fabric surface "L" of splint body 11. The X-strap may further comprise an intermediate inside patch 36 of nylon hook fasteners "H" located centrally between the diverging fastener tabs 33 and 34. Selected positioning of the distal fastener tabs 33, 34 on the splint body 11 allow the user to custom tension the X-strap 30, thereby creating a customized abduction force designed to maximize stabilization of the TMC joint at the base of the thumb. The exemplary X-strap 30 forms a continuous loop 37 around the mid-section (web space) of the thumb at or proximal to the first metacarpophalangeal joint, and is intended to effect independent abduction of the distal end of the metacarpal bone of the thumb. In alternative embodiments, a proximal end of the exemplary X-strap 30 is attached or secured to the thumb portion 14 adjacent the narrowed opening 15, but may not have a looped structure.

In addition to the above, the exemplary thumb splint 10 may further comprise a detachable and relocatable, ergonomically-curved stay pod 40 intended for custom placement on the splint body 11 at the base of the thumb portion 14. The exemplary stay pod 40 contains a rigid or semi-rigid metal stay sandwiched between opposing outside and inside fabric layers 41, 42. The inside layer 42 may comprise nylon hook fasteners "H" adapted to releasably mate with the outside loop fabric surface "L" of the splint body 11. In one embodiment, the metal stay (not shown) is removably inserted into a pocket formed between layers of the stay pod 40—the pocket being larger than the stay itself, such that the stay can shift left or right within the pocket to self-adjust to the location that best fits the anatomy of the user. This self-adjustment may minimize any discomfort caused by the metal stay at any given point proximate the TMC joint. In exemplary applications, the stay pod 40 is designed to be placed over the metacarpal bone of the thumb (e.g., at or distal to the TMC joint) near the thumb base to apply adduction pressure to help stabilize the TMC joint. The X-strap 30 and stay pod 40 combine to simultaneously and independently push and pull on opposite ends of the thumb's metacarpal bone, thereby enabling a wide range of support and custom stabilization for the TMC joint.

FIGS. 6-12 demonstrate one exemplary technique for applying the present orthopedic thumb splint 10 to the hand of the user. This technique is disclosed for purposes of illustration only, as the exemplary thumb splint 10 may be applied to and removed from the hand in a variety of ways. For example, various straps of exemplary thumb splint 10 may be tensioned and fastened to the splint body 11 by approaching the hand to which the splint 10 is applied either from the (above) dorsal side of the splinted hand or the (under) palmar side of the splinted hand.

Figure 6:
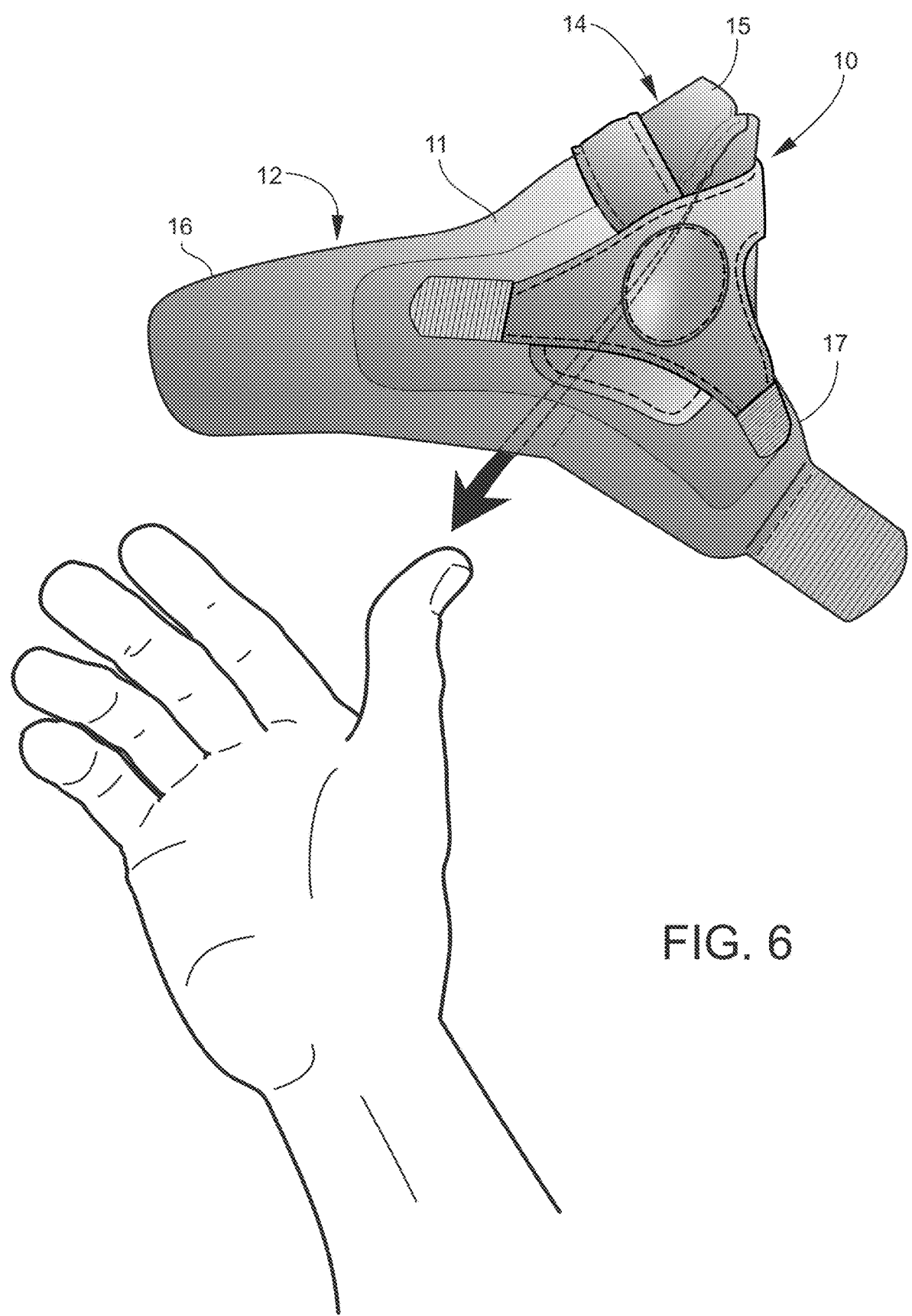
FIGS. 6 through 12 demonstrate one exemplary technique for applying the present orthopedic thumb splint to the hand of the user.
Figure 7:
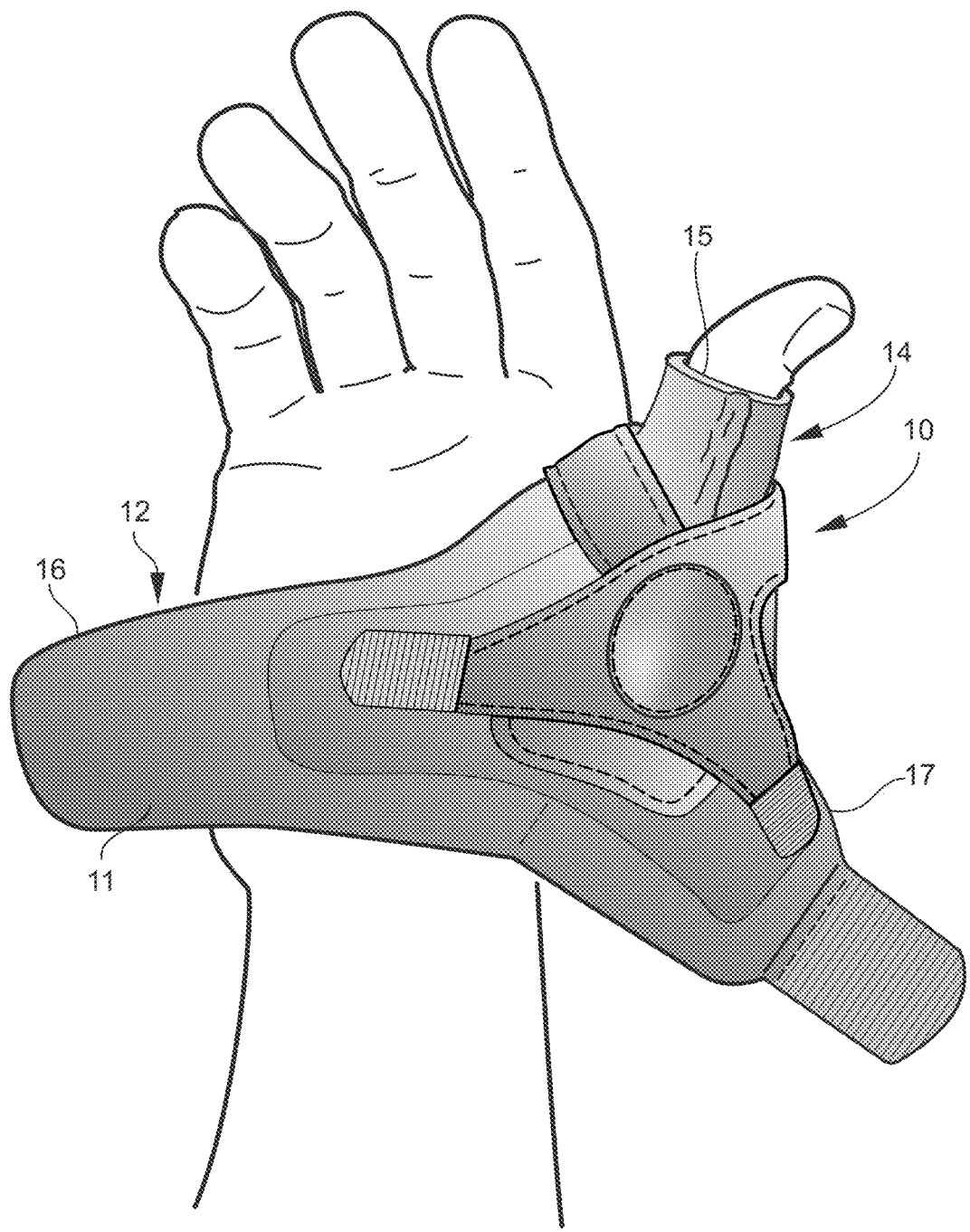
Figure 8:
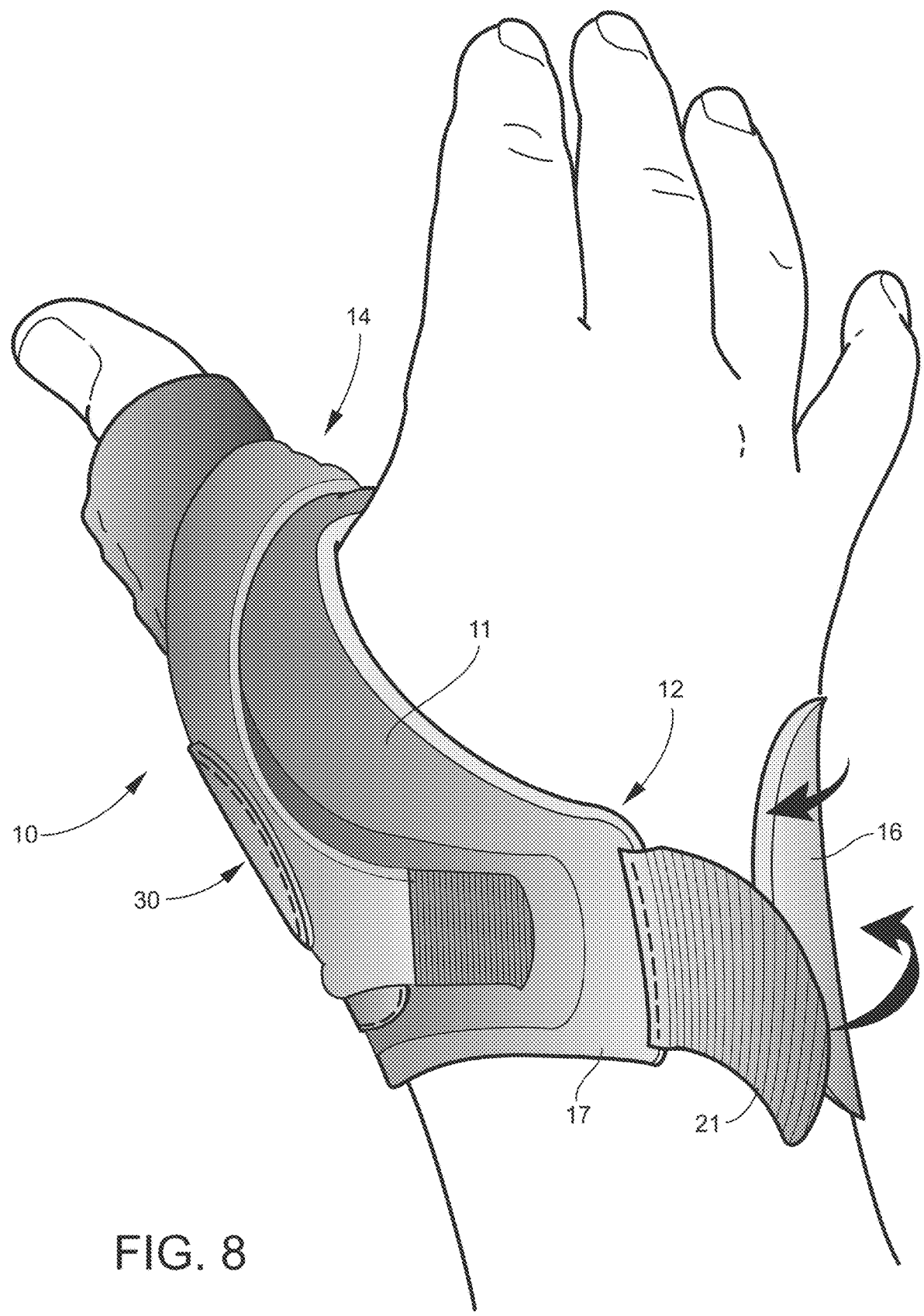
Figure 9:
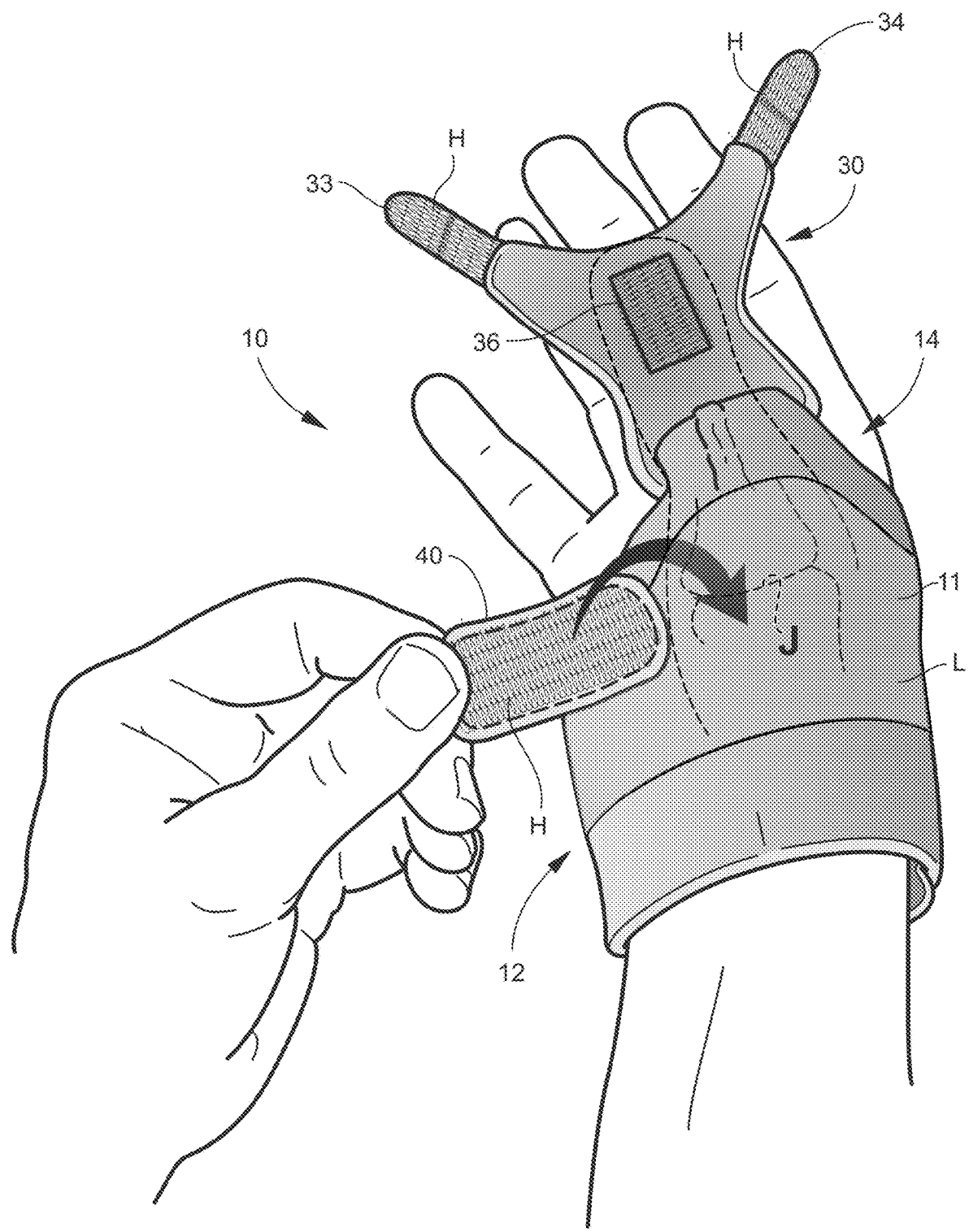

With the closure straps 16 and 17 extended, as shown in FIG. 6, the splint body 11 is applied to the hand such that the thumb of the user inserts through the narrowed opening 15 of the thumb portion 14. See FIG. 7. The splint body 11 is then secured to the hand by wrapping the closure straps 16, 17 around the wrist, as demonstrated in FIG. 8, and selectively tensioning the fit using the distal fastener tab 21 of strap 17. As shown in FIG. 9, the X-strap 30 is then lifted away from the splint body 11 in order to custom-locate the stay pod 40 at the base of the thumb portion 14. The hook fasteners "H" of stay pod 40 mate with the outside loop fabric surface "L" of the splint body 11, as previously described, to position the stay pod 40 proximate the TMC joint "J".

Figure 10:
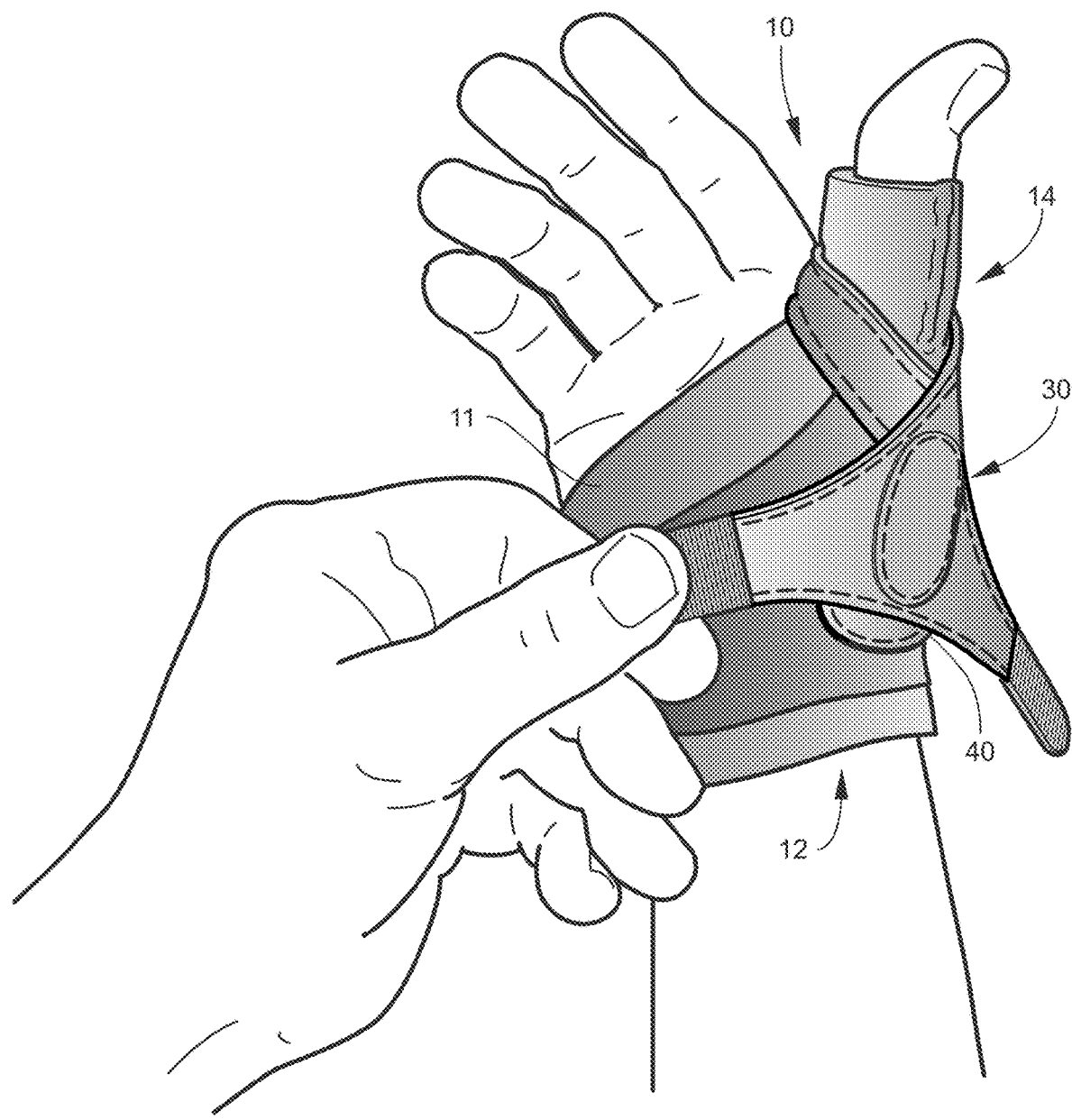
Figure 11:
Figure 12:
Figure 13:
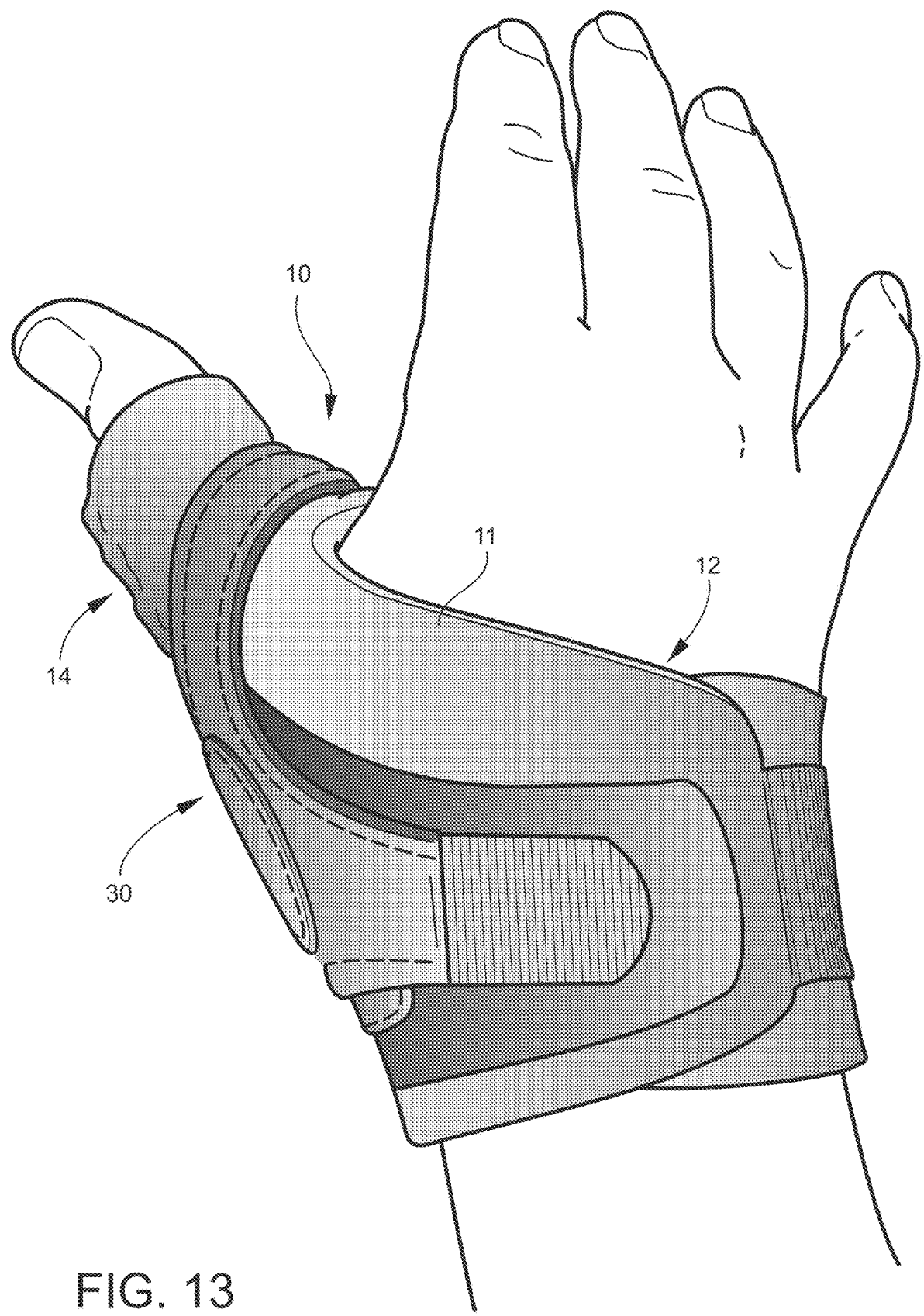
FIG. 13 is a further perspective view showing the exemplary orthopedic thumb splint positioned on the hand.

After the splint body 11 is comfortably secured to the hand, the X-strap 30 is pulled outwardly from the thumb portion 14 and downwardly over the stay pod 40, as demonstrated in FIG. 10, to slightly abduct the metacarpal bone thereby facilitating control of the MP joint—stabilizing the CMC joint and reduces its tendency to sublux. The midportion of the X-strap 30 is then anchored to the splint body 11 via inside hook patch 36 (FIG. 9) to hold the thumb in the desired position. As demonstrated in FIGS. 11 and 12, the diverging distal fastener tabs 33, 34 of X-strap 30 are then adjustably releasably attached to the splint body 11 via respective inside hook fasteners "H" (FIG. 9) in a manner that creates compression on the TMC joint "J" at the base of the thumb. This helps ensure that the joint "J" remains stable and properly aligned during normal use of the thumb. FIGS. 1, 2, and 13 show the exemplary orthopedic thumb splint 10 properly positioned on the hand of the user.

For the purposes of describing and defining the present invention it is noted that the use of relative terms, such as "substantially", "generally", "approximately", and the like, are utilized herein to represent an inherent degree of uncertainty that may be attributed to any quantitative comparison, value, measurement, or other representation. These terms are also utilized herein to represent the degree by which a quantitative representation may vary from a stated reference without resulting in a change in the basic function of the subject matter at issue.

Exemplary embodiments of the present invention are described above. No element, act, or instruction used in this description should be construed as important, necessary, critical, or essential to the invention unless explicitly described as such. Although only a few of the exemplary embodiments have been described in detail herein, those skilled in the art will readily appreciate that many modifications are possible in these exemplary embodiments without materially departing from the novel teachings and advantages of this invention. Accordingly, all such modifications are intended to be included within the scope of this invention as defined in the appended claims.

In the claims, any means-plus-function clauses are intended to cover the structures described herein as performing the recited function and not only structural equivalents, but also equivalent structures. Thus, although a nail and a screw may not be structural equivalents in that a nail employs a cylindrical surface to secure wooden parts together, whereas a screw employs a helical surface, in the environment of fastening wooden parts, a nail and a screw may be equivalent structures. Unless the exact language "means for" (performing a particular function or step) is recited in the claims, a construction under 35 U.S.C. § 112(f) [or 6th paragraph/pre-AIA] is not intended. Additionally, it is not intended that the scope of patent protection afforded the present invention be defined by reading into any claim a limitation found herein that does not explicitly appear in the claim itself.

What is claimed:

1. An orthopedic thumb splint adapted for stabilizing a carpometacarpal joint of a user, said orthopedic thumb splint comprising:
    a flexible fabric splint body comprising a wrist portion and a generally funnel-shaped thumb portion, said generally funnel-shaped thumb portion defining a narrowed opening for receiving a thumb of the user;
    a detachable and relocatable stay pod adapted for custom placement on said flexible fabric splint body at a base of said generally funnel-shaped thumb portion; and
    a thumb-abducting flexible X-strap secured to said flexible fabric splint body adjacent the narrowed opening of said generally funnel-shaped thumb portion, and comprising first and second diverging distal ends having respective inside surfaces, the inside surface of each of said first and second diverging distal ends comprising touch fasteners designed to releasably mate at respective first and second points of releasable attachment with complementary touch fasteners located on an outside surface of said flexible fabric splint body, whereby an adjustable abduction force is capable of being applied to the thumb of the user by pulling said X-strap outwardly from said generally funnel-shaped thumb portion and downwardly towards said wrist portion of said flexible fabric splint body, and then mating the touch fasteners of said first and second diverging distal ends and flexible fabric splint body to releasably attach said first and second diverging distal ends at a base of the thumb, such that said X-strap extends over said stay pod at the base of said generally funnel-shaped thumb portion.

2. The orthopedic thumb splint according to claim 1, wherein said wrist portion of said flexible fabric splint body comprises first and second cooperating flexible closure straps having respective free ends adapted to releasably wrap around a wrist of the user.

3. The orthopedic thumb splint according to claim 2, wherein said flexible fabric splint body comprises an inverted T-shaped non-stretch region located between said first and second closure straps, and extending upwardly along said generally funnel-shaped thumb portion towards the narrowed opening.

4. The orthopedic thumb splint according to claim 3, wherein said flexible fabric splint body is substantially stretchable in adjacent areas outside of said non-stretch region.

5. The orthopedic thumb splint according to claim 4, wherein said flexible fabric splint body comprises added padding in said non-stretch region.

6. The orthopedic thumb splint according to claim 2, wherein the free ends of said first and second closure straps comprise respective touch fasteners.

7. The orthopedic thumb splint according to claim 6, wherein said first closure strap comprises an intermediate inside patch of pre-hold touch fasteners spaced apart from its free end, and adapted to form a preliminary holding point when wrapping said first and second closure straps together around the wrist of the user.

8. The orthopedic thumb splint according to claim 7, wherein the free end of said first closure strap comprises a hook fastener tab.

9. The orthopedic thumb splint according to claim 1, wherein said X-strap further comprises a proximal looped end extending around said generally funnel-shaped thumb portion adjacent the narrowed opening.

10. The orthopedic thumb splint according to claim 9, wherein said X-strap is permanently affixed to said flexible fabric splint body on a web side of said generally funnel-shaped thumb portion.

11. The orthopedic thumb splint according to claim 10, wherein said X-strap further comprises an intermediate inside touch fastener located between said touch fasteners of said first and second diverging distal ends, and said intermediate inside touch fastener providing a third point of releasable attachment of said X-strap, wherein said first, second and third points of releasable attachment are spaced apart and separated from one another along a portion of said X-strap.

12. The orthopedic thumb splint according to claim 1, wherein said stay pod comprises a semi-rigid metal stay sandwiched between opposing outside and inside fabric layers.

13. The orthopedic thumb splint according to claim 12, wherein said stay pod comprises touch fasteners on said inside fabric layer adapted to releasably mate with complementary touch fasteners of said splint body.

14. The orthopedic thumb splint according to claim 1, wherein said first and second diverging distal ends of said X-strap comprise respective hook fastener tabs.

* * * * *